(12) United States Patent
Crassier et al.

(10) Patent No.: US 7,312,342 B2
(45) Date of Patent: Dec. 25, 2007

(54) PROCESS FOR THE PREPARATION OF (3-CYANO-1H-INDOL-7-YL) (4-(4-FLUOROPHENETHYL) PIPERAZIN-1-YL)-METHANONE AND SALTS THEREOF

(75) Inventors: Helene Crassier, Weiterstadt (DE); Uwe Eckert, Darmstadt (DE); Henning Boettcher, Darmstadt (DE); Andreas Bathe, Darmstadt (DE); Steffen Emmert, Weiterstadt (DE)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 736 days.

(21) Appl. No.: 10/466,991

(22) PCT Filed: Dec. 21, 2001

(86) PCT No.: PCT/EP01/15240

§ 371 (c)(1),
(2), (4) Date: Jul. 23, 2003

(87) PCT Pub. No.: WO02/059092

PCT Pub. Date: Aug. 1, 2002

(65) Prior Publication Data

US 2004/0063723 A1    Apr. 1, 2004

(30) Foreign Application Priority Data

Jan. 23, 2001  (DE) .............................. 101 02 944

(51) Int. Cl.
*C07D 209/04* (2006.01)

(52) U.S. Cl. ........................ 548/469; 548/416; 548/452
(58) Field of Classification Search ................ 548/416, 548/452, 469
See application file for complete search history.

(56) References Cited

OTHER PUBLICATIONS

T. Owa et al.: "Discovery of Novel Antitumor Sulfonamides Targeting G1 Phase of the Cell Cycle" J. Med. Chem., vol. 42, No. 19, 1999, pp. 3789-3799, XP002193774.
S. Swaminathan et al.: "N-Mannich Bases of 3-Substituted Indoles and Alkylation with Some N-Indolylmethyltrimethylammonium Iodides" J. Org. Chem., vol. 23, 1958, pp. 707-711, XP001063047.
F. Santanelo et al.: "A convenient synthesis of 9-hydroxy-3, 4,5, 6-tetrahydro-1H-azepino ' 5, 4, 3-cd! indole form 7-methoxyindole" Synth. Commun. , vol. 23, No. 19, 1993, pp. 2717-2726, XP001063048.
D. Sowmithran, K.J. Rajendra Prasad: "Heterocycles: Part 5—Synethesis of Carbazolyl-1-oxypropanolamine" Indian J. Chem. Sect. B, vol. 26, No. 1-12, 1987, pp. 277-278 XP001057373.

*Primary Examiner*—James O. Wilson
*Assistant Examiner*—Paul V. Ward
(74) *Attorney, Agent, or Firm*—Millen, White, Zelano, Branigan, P.C.

(57) ABSTRACT

The present invention relates to a process for the preparation of (3-cyano-1H-indol-7-yl)[4-(4-fluorophenethyl)piperazin-1-yl]-methanone and salts thereof, characterised in that an indole ester of the formula II in which R is as defined in Claim 1, is converter into 3-cyano-1H-indole-7-carboxylic acid via steps (1) to (4) according to Claim 1, and this is reacted with 1-[2-(4-fluorophenyl)ethyl]piperazine of salts thereof to give the product.

26 Claims, No Drawings

PROCESS FOR THE PREPARATION OF (3-CYANO-1H-INDOL-7-YL)(4-(4-FLUOROPHENETHYL)PIPERAZIN-1-YL)-METHANONE AND SALTS THEREOF

The invention relates to a process for the preparation of (3-cyano-1H-indol-7-yl)[4-(4-fluorophenethyl)piperazin-1-yl]methanone of the formula I,

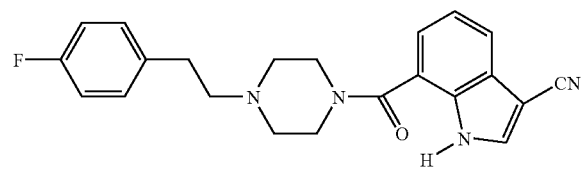

and salts thereof, and of intermediates in the synthesis.

The compound (3-cyano-1H-indol-7-yl)[4-(4-fluorophenethyl)piperazin-1-yl]methanone and the corresponding physiologically acceptable salts surprisingly have selective affinity to $5\text{-HT}_{2A}$ receptors. In particular, they are selective $5\text{-HT}_{2A}$ antagonists.

$5\text{-HT}_{2A}$ antagonists exhibit clinically antipsychotic activity with no or minimal side effects and are correspondingly regarded as antipsychotics having few side effects. In addition, they can be used in the treatment of neurological disorders attributable to disturbances in serotonergic transmission, such as depression, anxiety states, panic illnesses, obsessive-compulsive disorders, pain, sleep disturbances, sleeplessness, eating disorders, such as anorexia nervosa, bulimia, addiction behaviour, dependence on certain addiction-causing substances, such as LSD and MDMA, cardiovascular disorders, such as various angina diseases, Raynaud's syndrome, intermittent claudication, cardiac or peripheral vascular spasms, fibromyalgia, cardiac arrhythmia and thrombotic illnesses, since the substances inhibit platelet aggregation. In combination with classical or atypical neuroleptics, the side effects induced by the neuroleptics can be suppressed. Owing to the reduction in ocular pressure, the substances can also be employed in glaucoma therapy. Toxic symptoms caused by poisoning with, for example, ergovalin, can be suppressed using the substances.

The compounds can therefore be used as medicament active ingredients in human and veterinary medicine. They can furthermore be used as intermediates for the preparation of further medicament active ingredients.

Since (3-cyano-1H-indol-7-yl)[4-(4-fluorophenethyl)piperazin-1-yl]methanone and salts thereof are very highly promising as medicaments, the preparation is of extremely high interest.

The object of the present invention was therefore to find a novel and effective synthesis variant for the $5\text{-HT}_{2A}$ receptor antagonists.

The invention therefore relates to a process for the preparation of (3-cyano-1H-indol-7-yl)[4-(4-fluorophenethyl)piperazin-1-yl]methanone of the formula I,

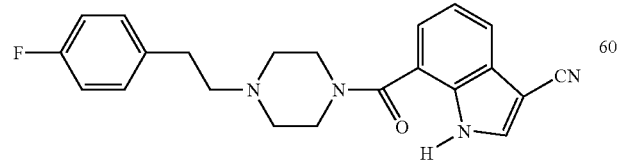

and salts thereof, characterised in that (1) an indole ester of the formula II

in which
R is an alkyl group having from 1 to 6 carbon atoms or arylalkyl, is formylated, (2) the formyl ester of the formula III

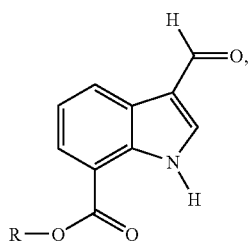

in which R is as defined above,
formed from (1) is reacted with hydroxylamine to give an oxime derivative of the formula IV

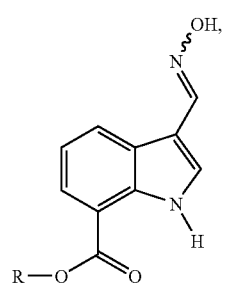

in which R is as defined above, (3) the oxime of the formula IV is converted into a cyanoindole ester of the formula V

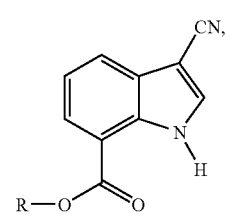

in which R has one of the meanings indicated above, (4) the ester of the formula V is saponified to give 3-cyano-1H-indole-7-carboxylic acid, (5) the 3-cyano-1H-indole-7-carboxylic acid is reacted with 1-[2-(4-fluoro-phenyl)ethyl]piperazine or salts thereof to give the compound of the formula I, and (6) the resultant base of the formula I is converted into one of its salts by treatment with an acid.

The substituent R in the formulae II to VI is an alkyl group having from 1 to 6 carbon atoms or an arylalkyl group.

The alkyl group preferably has 1, 2, 3 or 4 carbon atoms and is therefore, for example, methyl, ethyl, n-propyl, isopropyl, n-butyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore trifluoromethyl or pentafluoroethyl.

Arylalkyl is alternatively —$(CH_2)_o$—Ar, where Ar is preferably phenyl or naphthyl, and o can be 0, 1 or 2. Arylalkyl is, in particular, benzyl, phenylethyl or naphthylmethyl, particularly preferably benzyl.

R is preferably methyl or ethyl, particularly preferably ethyl.

The indole esters of the formula II are commercially available or can be prepared by known synthetic methods. The preparation can, for example, be carried out starting from 3-methyl-2-nitrobenzoic acid, which is commercially available, by the following reactions:
(1) esterification of 3-methyl-2-nitrobenzoic acid,
(2) reaction with an N,N-dimethylformamide acetal to give a 3-(2-dimethylaminovinyl)-2-nitrobenzoic acid ester, and
(3) subsequent palladium-catalysed ring closure reaction to give the indole ester of the formula II.

Suitable indole esters of the formula II are, in particular, methyl 1H-indole-7-carboxylate, ethyl 1H-indole-7-carboxylate, tert-butyl 1H-indole-7-carboxylate and benzyl 1H-indole-7-carboxylate. The synthesis according to the invention is particularly preferably carried out using ethyl 1H-indole-7-carboxylate.

Suitable N,N-dimethylformamide acetals are, for example, N,N-dimethylformamide bis[2-(trimethylsilyl) ethyl]acetal, N,N-dimethylformamide dibenzyl acetal, N,N-dimethylformamide dibutyl acetal, N,N-dimethylformamide di-tert-butyl acetal, N,N-dimethylformamide diethyl acetal, N,N-dimethylformamide diisopropyl acetal, N,N-dimethylformamide dimethyl acetal, N,N-dimethylformamide dineopentyl acetal, N,N-dimethylformamide dipropyl acetal and N,N-dimethylformamide ethylene acetal. Particular preference is given to N,N-dimethylformamide diethyl acetal and N,N-dimethylformamide dimethyl acetal.

The palladium-catalysed cyclisation reaction is carried out analogously to the method of Leimgruber-Batcho [Clark R. D. et al, Heterocycles, 1984, 22, 195-221, Batcho D. et al, Organic Synthesis, 1985, 63, 214-225].

The reaction conditions selected are known from the literature. However, it is also possible to use other processes known from the literature, which are not explained in greater detail here, for the preparation of compounds of the formula II (lit.: Houben-Weyl, Methoden der Organ. Chemie [Methods of Organic Chemistry], Georg-Thieme-Verlag, Stuttgart).

The formylation of a compound of the formula II to give a formyl ester of the formula III, in which R has one of the meanings indicated above, is carried out analogously to the method of Vilsmeyer-Haack [Jutz C. et al., Iminium Salts in Organic Chemistry Part I, New York, John Wiley & Sons Inc., 1976, pp. 234 ff, pp. 237 ff]. The reaction is preferably carried out in an aprotic polar solvent and at reaction temperatures between 0° and 50° and with heating to from 100° to 130° C. Particularly preferred solvents are dimethylformamide (DMF) and mixtures of DMF with aromatic hydrocarbons, such as benzene, toluene or xylene, or with further amides, such as N-methylpyrrolidone (NMP).

The formylation is particularly preferably carried out in DMF in the presence of $POCl_3$.

Suitable formylindole esters of the formula III are, in particular, 7-methoxycarbonyl-3-indolecarboxaldehyde, 7-ethoxycarbonyl-3-indolecarboxaldehyde, 7-tert-butoxycarbonyl-3-indolecarboxaldehyde and 7-benzyloxycarbonyl-3-indolecarboxaldehyde. The synthesis according to the invention is particularly preferably carried out using 7-ethoxycarbonyl-3-indolecarboxaldehyde.

The oximation of the compounds of the formula III, as described above, is carried out under standard conditions (lit.: Kurtz P., Houben-Weyl, Methoden der Organ. Chemie [Methods of Organic Chemistry], Vol. VIII, Georg-Thieme-Verlag, Stuttgart).

The oximation is particularly preferably carried out in polar aprotic solvents, such as DMF, benzene, toluene, xylene or NMP, at temperatures between 0° and 50°, in particular at room temperature.

The preparation of the cyanoindole esters of the formula V, as described above, is carried out by treatment with acid. Suitable acids are, for example, inorganic acids, such as hydrochloric acid, sulfuric acid or phosphoric acid, or organic acids, such as formic acid, acetic acid, p-toluenesulfonic acid or methanesulfonic acid. The reaction is particularly preferably carried out in high-boiling aprotic solvents, such as DMF or NMP, or mixtures thereof with aprotic solvents, at temperatures between 20° and 100°, in particular at 50° C.

In a particular embodiment of the process, steps (1) to (3) are carried out in situ, i.e. in a one-pot process analogously to Liebscher J. et al, Z. Chem. 1983, 23, 214-215, without the intermediates being isolated. The one-pot process gives better yields compared with the stepwise synthesis.

The saponification of the compounds of the formula V to give 3-cyano-1H-indole-7-carboxylic acid is carried out under standard conditions (lit.: Houben-Weyl, Methoden der Organ. Chemie [Methods of Organic Chemistry], Georg-Thieme-Verlag, Stuttgart).

The saponification is particularly preferably carried out using KOH in methanol at room temperature.

As an alternative to chemical saponification, the ester cleavage can also be carried out enzymatically with the aid of esterases. Suitable esterases are, for example, *Bacillus* sp. esterase, *Bacillus stearothermophilus* esterase, *Candida lipolytica* esterase, *Mucor miehei* esterase, horse liver esterase, *Saccaromyces cerevisiae* esterase, pig's liver esterase, *Thermoanaerobium brockii* esterase and pig's liver esterase isoenzyme 1. The esterases may also be employed in immobilised form. Commercial immobilised esterases are, for example, pig's liver esterase (PLE) immobilised on Eupergit® C or on oxirane-acrylic beads.

Enzymatic reactions are preferably carried out in aqueous buffer systems, but other solvents, in particular alcohols, such as ethanol, may also be present.

The reaction of 3-cyano-1H-indole-7-carboxylic acid with 1-[2-(4-fluorophenyl)ethyl]piperazine or one of the salts, in particular, with 1-[2-(4-fluorophenyl)ethyl]piperazine dihydrochloride, is carried out by methods as are known from the literature for the acylation of amines [Houben-Weyl, I.c., Volume 15/II, pages 1 to 806 (1974)]. However, it is also possible to react the compounds in the presence of an inert solvent. Examples of suitable solvents are hydrocarbons, such as benzene, toluene and xylene; ketones, such as acetone and butanone; alcohols, such as methanol, ethanol, isopropanol and n-butanol; ethers, such as tetrahydrofuran (THF) and dioxane; amides, such as dimethylformamide (DMF) or N-methylpyrrolidone; nitriles, such as acetonitrile, if desired also mixtures of these solvents with one another or mixtures with water. The addition of an acid-binding agent, for example an alkali or alkaline earth metal hydroxide, carbonate or bicarbonate or of another salt of a weak acid of the alkali or alkaline earth metals, preferably of potassium, sodium or calcium, or the addition of an organic base, such as triethylamine, dimethylaniline, pyridine or quinoline, or of an excess of a piperazine derivative, may be favourable. Depending on the conditions used, the reaction temperature is between about 0° and 150°, normally between 20° and 130°.

Instead of the 3-cyano-1H-indole-7-carboxylic acid, it is also possible to employ derivatives of this acid, preferably the preactivated carboxylic acid, or a corresponding carboxylic acid halide, a symmetrical or mixed anhydride or an active ester of 3-cyano-1H-indole-7-carboxylic acid. Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example by addition of HOBt or N-hydroxysuccinimide.

The compound 1-[2-(4-fluorophenyl)ethyl]piperazine and salts thereof are known and can be prepared by conventional processes which are known to the person skilled in the art. A description of the preparation is disclosed, for example, in DE 2855703.

A resultant base of the formula I can be converted into the associated acid-addition salt using an acid. Suitable acids for this reaction are those which give physiologically acceptable salts. Thus, it is possible to use inorganic acids, for example sulfuric acid, hydrohalic acids, such as hydrochloric acid or hydrobromic acid, phosphoric acids, such as orthophosphoric acid, nitric acid or sulfamic acid, furthermore organic acids, in detail aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids and laurylsulfuric acid.

In a preferred embodiment, the salt formation is carried out in a solvent mixture of acetone/water in a ratio of between 5:1 and 4:1 by precipitation using hydrochloric acid (37%). (3-Cyano-1H-indol-7-yl)[4-(4-fluorophenethyl)piperazin-1-yl]methanone, hydrochloride, is formed.

In a further embodiment of the process according to the invention, the cyanoindole ester of the formula V can be reacted directly, without prior saponification to 3-cyano-1H-indole-7-carboxylic acid, with 1-[2-(4-fluorophenyl)ethyl]piperazine or a corresponding salt by chemical or biochemical aminolysis.

The chemical aminolysis can be carried out, for example, by the method of Menger F. M. et al., J. Am. Chem. Soc. 1969, 91, 5346-9.

The biochemical aminolysis can be carried out, for example, by reaction of a compound of the formula V with 1-[2-(4-fluorophenyl)ethyl]piperazine or one of the corresponding salts in the presence of a lipase or an antibody. The biochemical aminolysis can be carried out, for example, by the method of Gotor V. et al., Bioorg. Med. Chem. 1999, 7, 2189-2197.

The invention therefore likewise relates to a process for the preparation of (3-cyano-1H-indol-7-yl)[4-(4-fluorophenethyl)piperazin-1-yl]methanone of the formula I

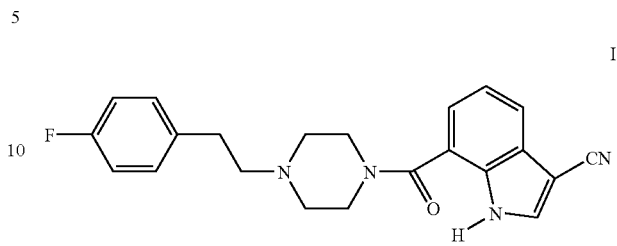

and salts thereof, characterised in that
(1) an indole ester of the formula II

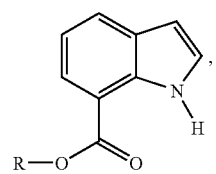

in which
R is an alkyl group having from 1 to 6 carbon atoms or arylalkyl, is formylated,
(2) the formyl ester of the formula III

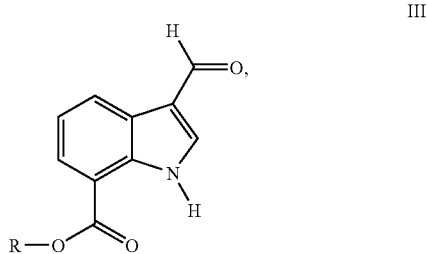

in which R is as defined above,
formed from (1) is reacted with hydroxylamine to give an oxime derivative of the formula IV

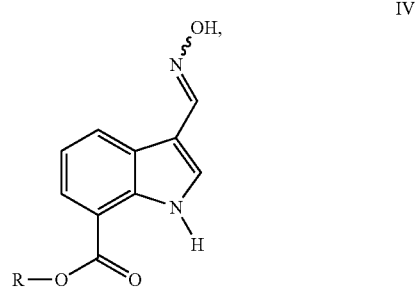

in which R is as defined above, (3) the oxime of the formula IV is converted into a cyanoindole ester of the formula V

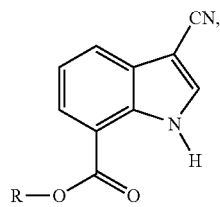

in which R has one of the meanings indicated above,
(4) the ester of the formula V is converted into the compound of the formula I by aminolysis using 1-[2-(4-fluorophenyl)ethyl]piperazine or one of the salts, and
(5) the resultant base of the formula I is converted into one of its salts by treatment with an acid.

In a further embodiment of the process according to the invention, the compound 3-cyano-1H-indole-7-carboxylic acid can be prepared by halogenation of an indole ester of the formula II

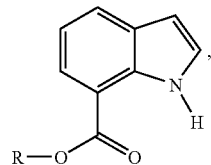

as described above to give a compound of the formula VI

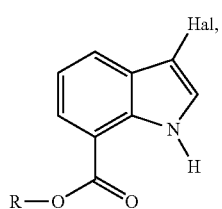

in which R is an alkyl group having from 1 to 6 carbon atoms or arylalkyl and
Hal is Cl, Br or I, followed by cyanation.

The halogenation of the compounds of the formula II, as described above, is carried out under standard conditions (lit.: Houben-Weyl, Methoden der Organ. Chemie [Methods of Organic Chemistry], Georg-Thieme-Verlag, Stuttgart) or analogously to Heterocycles, 1986, 24, 2879-85, ibid. 1989, 29, 1663-7; J. Am. Chem. Soc. 1985, 107, 2943-5; J. Org. Chem. 1993, 58, 2058-60, or J. Chem. Soc., Perkin Trans. 1, 1989, 2009-15.

The bromination or iodination in the 3-position of the indole can likewise be carried out analogously to Bocchi et al. Synthesis 1982, 1096-1097.

Examples of suitable solvents for the halogenation are hydrocarbons, such as benzene, toluene and xylene; halogenated hydrocarbons, such as dichloromethane and chloroform; ketones, such as acetone and butanone; alcohols, such as methanol, ethanol, isopropanol and n-butanol; ethers, such as tetrahydrofuran (THF) and dioxane; amides, such as dimethylformamide (DMF) and N-methylpyrrolidone; nitriles, such as acetonitrile, and if desired mixtures of these solvents with one another.

Compounds prepared in accordance with the invention by halogenation are, for example, methyl 3-chloro-1H-indole-7-carboxylate, methyl 3-bromo-1H-indole-7-carboxylate, methyl 3-iodo-1H-indole-7-carboxylate, ethyl 3-chloro-1H-indole-7-carboxylate, ethyl 3-bromo-1H-indole-7-carboxylate, ethyl 3-iodo-1H-indole-7-carboxylate, tert-butyl 3-chloro-1H-indole-7-carboxylate, tert-butyl 3-bromo-1H-indole-7-carboxylate, tert-butyl 3-iodo-1H-indole-7-carboxylate, benzyl 3-chloro-1H-indole-7-carboxylate, benzyl 3-bromo-1H-indole-7-carboxylate and benzyl 3-iodo-1H-indole-7-carboxylate. The use of ethyl 3-bromo-1H-indole-7-carboxylate or ethyl 3-iodo-1H-indole-7-carboxylate is particularly suitable in accordance with the invention.

The substitution of the halogen group of the compounds of the formula VI by the cyano group is carried out analogously to the method of Cassar L. et al., Adv. Chem. Ser. 1974, 132, 252-73, with nickel catalysis or analogously to the method of Sakamoto T. et al, J. Chem. Soc., Perkin Trans. 1 1999, 16, 2323-2326, or Chatani N. et al, J. Org. Chem. 1986, 51, 4714-16, with palladium catalysis.

The cyano group is particularly preferably introduced with palladium catalysis.

The invention therefore likewise relates to a process for the preparation of (3-cyano-1H-indol-7-yl)[4-(4-fluorophenethyl)piperazin-1-yl]methanone of the formula I

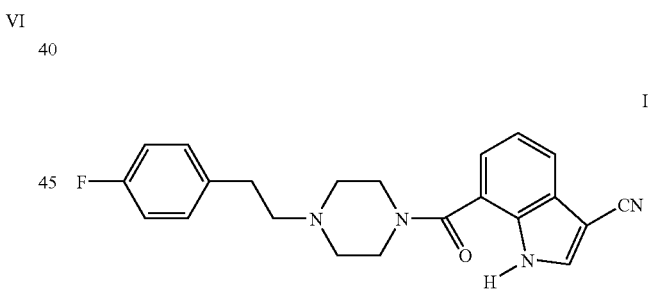

and salts thereof, characterised in that
(1) an indole ester of the formula II

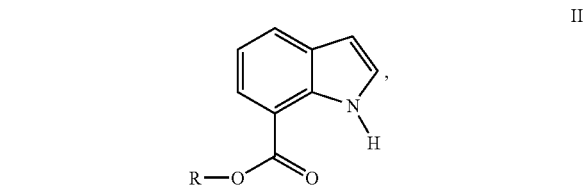

in which
R is an alkyl group having from 1 to 6 carbon atoms or arylalkyl, is halogenated, (2) the halogen group of the ester of the formula VI

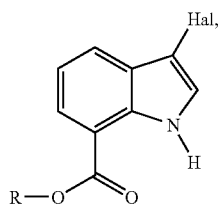

VI in which R and Hal are as defined above,
formed from (1) is converted into a cyano group, with the ester being saponified to 3-cyano-1H-indole-7-carboxylic acid at the same time,
(3) the 3-cyano-1H-indole-7-carboxylic acid is reacted with 1-[2-(4-fluorophenyl)ethyl]piperazine or salts thereof to give the compound of the formula I, and
(4) the resultant base of the formula I is converted into one of its salts by treatment with an acid.

A further aspect of the invention relates to compounds of the formula IV

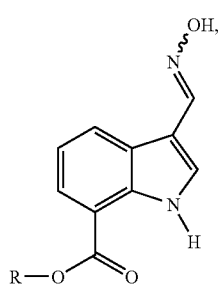

IV in which R is an alkyl group having from 1 to 6 carbon atoms or arylalkyl, and salts thereof.

Alkyl and arylalkyl have one of the meanings indicated above.

Compounds of the formula IV may occur in two isomeric forms, compounds of the formulae IVa and IVb. The general formula IV covers the individual isomers of the formulae IVa and IVb as well as mixtures thereof.

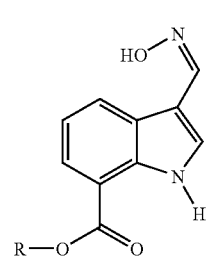

IVa

-continued

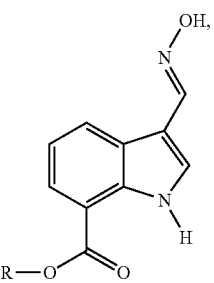

IVb in which R has one of the meanings indicated above.

Preferred compounds of the formula IV are
methyl 3-hydroxyimino-1H-indole-7-carboxylate,
ethyl 3-hydroxyimino-1H-indole-7-carboxylate,
tert-butyl 3-hydroxyimino-1H-indole-7-carboxylate and
benzyl 3-hydroxyimino-1H-indole-7-carboxylate, where both the Z- and E-forms and mixtures of these are included.

Particularly preferred compounds of the formula IV are
ethyl (Z)-3-hydroxyimino-1H-indole-7-carboxylate,
ethyl (E)-3-hydroxyimino-1H-indole-7-carboxylate and E/Z mixtures.

A salt of the compounds of the formula IV can be prepared by the methods described above for compounds of the formula I.

The compounds of the formula IV are valuable intermediates in the synthesis of (3-cyano-1H-indol-7-yl)[4-(4-fluorophenethyl)piperazin-1-yl]methanone and salts thereof, as described above.

A further aspect of the invention relates to compounds of the formula V

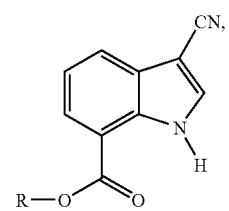

V in which R is an alkyl group having from 1 to 6 carbon atoms or arylalkyl, and salts thereof.

Alkyl and arylalkyl have one of the meanings indicated above.

Preferred compounds of the formula V are
methyl 3-cyano-1H-indole-7-carboxylate,
ethyl 3-cyano-1H-indole-7-carboxylate,
tert-butyl 3-cyano-1H-indole-7-carboxylate and
benzyl 3-cyano-1H-indole-7-carboxylate, and salts thereof.

The process according to the invention is particularly preferably carried out using ethyl 3-cyano-1H-indole-7-carboxylate.

A salt of the compounds of the formula V can be prepared by the methods described above for compounds of the formula I.

The compounds of the formula V are valuable intermediates in the synthesis of (3-cyano-1H-indol-7-yl)[4-(4-fluorophenethyl)piperazin-1-yl]methanone and salts thereof, as described above.

The invention likewise relates to the compound 3-cyano-1H-indole-7-carboxylic acid and salts thereof.

A further aspect of the invention relates to compounds of the formula VI

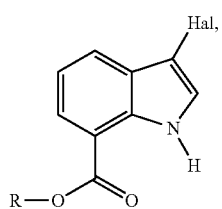

VI in which R is an alkyl group having from 1 to 6 carbon atoms or arylalkyl, and Hal is Cl, Br or I and salts thereof.

Alkyl and arylalkyl have one of the meanings indicated above.

Preferred compounds of the formula VI are methyl 3-bromo-1H-indole-7-carboxylate, ethyl 3-bromo-1H-indole-7-carboxylate, tert-butyl 3-bromo-1H-indole-7-carboxylate and benzyl 3-bromo-1H-indole-7-carboxylate, methyl 3-iodo-1H-indole-7-carboxylate, ethyl 3-iodo-1H-indole-7-carboxylate, tert-butyl 3-iodo-1H-indole-7-carboxylate and benzyl 3-iodo-1H-indole-7-carboxylate, and salts thereof.

The process according to the invention is particularly preferably carried out using ethyl 3-bromo-1H-indole-7-carboxylate or ethyl 3-iodo-1H-indole-7-carboxylate.

A salt of the compounds of the formula VI can be prepared by the methods described above for compounds of the formula I.

The compounds of the formula VI are valuable intermediates in the synthesis of (3-cyano-1H-indol-7-yl)[4-(4-fluorophenethyl)piperazin-1-yl]methanone and salts thereof, as described above.

Even without further details, it is assumed that a person skilled in the art will be able to utilise the above description in the broadest scope. The preferred embodiments should therefore merely be regarded as descriptive disclosure which is absolutely not to be regarded as limiting in any way.

All temperature data above and below are given in ° C. In the following examples, "conventional work-up" means that water is added if necessary, the mixture is adjusted, if necessary, to a pH of between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

EXAMPLE 1

1.1. Methyl 3-formylindole-7-carboxylate 2.9 ml of phosphorus oxychloride are added slowly to 7 ml of N,N-dimethylformamide in a nitrogen atmosphere (formylation solution). 5 g (0.029 mol) of methyl indole-7-carboxylate are dissolved in 7 ml of DMF and added slowly to the formylation solution, during which the temperature does not rise above 30 degrees. The mixture is then warmed at 100° for one hour. After cooling, the mixture is poured into water and neutralised using sodium hydroxide solution, and the deposited crystals are filtered off with suction. m.p. 154°. Yield 5.3 g (89.9% of theory).

1.2. Methyl 3-(hydroxyiminomethyl)indole-7-carboxylate 5 g of methyl 3-formylindole-7-carboxylate (0.024 mol) are added to a solution of 0.03 mol of hydroxylammonium hydrochloride in dimethylformamide. The reaction mixture is heated at 125° for one hour and subjected to conventional work-up, giving 5.1 g of methyl 3-(hydroxyiminomethyl)indole-7-carboxylate.

1.3. Methyl 3-cyanoindole-7-carboxylate 5 g of methyl 3-(hydroxyiminomethyl)indole-7-carboxylate are suspended in 20 ml of toluene, 1 ml of sulfonyl chloride is added, and the mixture is refluxed for one hour. Evaporation and extraction with ethyl acetate give 4.5 g of methyl cyanoindole-7-carboxylate, m.p. 212°.

1.4. 3-Cyanoindole-7-carboxylic acid 4.5 g (0.022 mol) of methyl cyanoindole-7-carboxylate are suspended in 100 ml of methanol, and a solution of 30 ml of sodium hydroxide solution (w=32%) in 30 ml of water is added at room temperature. Stirring over-night gives a virtually clear solution, which is filtered and evaporated. Water is added to the residue until a clear solution is formed, and the mixture is adjusted to pH=2 using concentrated hydrochloric acid with ice-cooling. The white crystals are filtered off with suction and dried for 2 hours under reduced pressure, giving 4 g of 3-cyanoindole-7-carboxylic acid (97.7% of theory); m.p. 317.5-318.5°.

1.5. 7-{4-[2-(4-Fluorophenyl)ethyl]piperazine-1-carbonyl}-1H-indole-3-carbonitrile 5 g (0.027 mol) of 3-cyanoindole-7-carboxylic acid are dissolved in 40 ml of hot N-methylpyrrolidone, the solution is cooled to 40°, and 7.6 g (0.027 mol) of N,N-carbonyldiimidazole are added. The mixture is stirred at room temperature for a further one hour. A suspension of 1-(2-(4-fluorophenyl)ethyl)piperazine dihydrochloride in 40 ml of N-methylpyrrolidone is subsequently poured in. After 5 minutes, a clear solution is formed and just afterwards white crystals deposit. The mixture is stirred overnight at room temperature. The crystals are filtered off with suction, washed and dried, giving 5 g of 7-{4-[2-(4-fluorophenyl)ethyl]piperazin-1-carbonyl}-1H-indole-3-carbonitrile as the free base having a melting point (m.p.) of 192.0-193.5°.

The chemical names 7-{4-[2-(4-fluorophenyl)ethyl]piperazine-1-carbonyl}-1H-indole-3-carbonitrile and (3-cyano-1H-indol-7-yl)[4-(4-fluorophenethyl)-piperazin-1-yl]methanone are synonymous.

1.6. 7-{4-[2-(4-Fluorophenyl)ethyl]piperazin-1-carbonyl}-1H-indole-3-carbonitrile, hydrochloride 2.1 g of the free base obtained in accordance with 1.5 are heated in 50 ml of acetone, and water is added until a clear solution is formed. A mixture of 0.6 ml of hydrochloric acid (w=37%) and 1.2 ml of acetone is then stirred in. The mixture is subsequently evaporated to half the volume in a rotary evaporator. The precipitated hydrochloride is filtered off with suction, washed with acetone and diethyl ether and dried, giving 1.6 g of 7-{4-[2-(4-fluorophenyl)ethyl]piperazin-1-carbonyl}-1H-indole-3-carbonitrile, hydrochloride (69% of theory), decomposition range 314-319°.

EXAMPLE 2

2.1. Methyl 3-cyanoindole-7-carboxylate 9.1 g of phosphoryl chloride are added to 30 ml of dimethylformamide with ice cooling at a reaction temperature of 20-30°. A solution of 8 g of methyl indole-7-carboxylate in dimethylformamide is added dropwise, during which the temperature rises to 40°. After one hour at 125°, the solution is added dropwise while still hot to a solution of 6.3 g of hydroxylammonium chloride in 40 ml of dimethylformamide, and the mixture is stirred at 120° C. for a further 15 minutes. The mixture is poured into water, extracted with ethyl acetate, filtered through neutral aluminium oxide and evaporated, giving 4.5 g of methyl 3-cyanoindole-7-carboxylate having a melting range of 212-213.5° (48.9% of theory).

The further reaction is carried out analogously to Example 1.4. to 1.6.

EXAMPLE 3

3.1. Ethyl 3-bromoindole-7-carboxylate 12 g of pyridine hydrobromide perbromide are added to a solution of 5 g of ethyl indole-7-carboxylate in 50 g of pyridine. The reaction mixture is warmed to 30-50° and stirred until the conversion is complete (from about 3 to 10 hours).

Conventional work-up gives ethyl 3-bromoindole-7-carboxylate.

3.2. 3-Cyanoindole-7-carboxylic acid 7 g of ethyl 3-bromoindole-7-carboxylate are dissolved in 70 g of NMP, and 4 g of CuCN are added. The mixture is heated to 100-140° C. with stirring. After 3 hours, the mixture is subjected to conventional work-up, giving 3-cyanoindole-7-carboxylic acid.

The further reaction of the 3-cyanoindole-7-carboxylic acid is carried out analogously to Example 1.5. to 1.6.

What is claimed is:

1. An oxime compound of formula IV

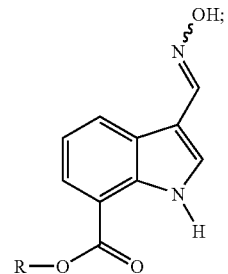

in which
R is an alkyl group having from 1 to 6 carbon atoms or arylalkyl,
or a salt thereof.

2. A cyanoindole ester compound of formula V

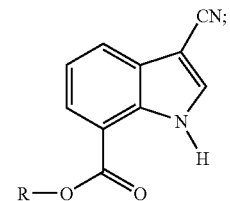

in which
R is an alkyl group having from 1 to 6 carbon atoms or arylalkyl,
or a salt thereof.

3. The compound 3-Cyano-1H-indole-7-carboxylic acid or a salt thereof.

4. A compound of formula VI

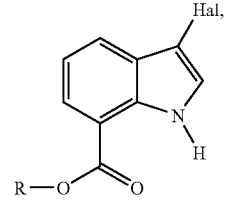

in which
R is an alkyl group having from 1 to 6 carbon atoms or arylalkyl, and
Hal is Cl, Br or I,
or a salt thereof.

5. A compound of the formula

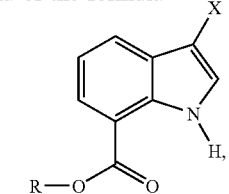

wherein

X is —CH=N—OH, CN, or Hal,

Hal is Cl, Br or I,

R is an alkyl group having from 1 to 6 carbon atoms or arylalkyl, or when X is CN, R can also be H, or a salt thereof.

6. A compound according to claim 1, wherein R is an alkyl group having from 1 to 6 carbon atoms.

7. A compound according to claim 2, wherein R is an alkyl group having from 1 to 6 carbon atoms.

8. A compound according to claim 4, wherein R is an alkyl group having from 1 to 6 carbon atoms.

9. A compound according to claim 5, wherein R is an alkyl group having from 1 to 6 carbon atoms.

10. A compound according to claim 1, wherein R is —(CH$_2$)$_o$—Ar wherein Ar is phenyl or naphthyl and o is 0, 1, or 2.

11. A compound according to claim 2, wherein R is —(CH$_2$)$_o$—Ar wherein Ar is phenyl or naphthyl and o is 0, 1, or 2.

12. A compound according to claim 4, wherein R is —(CH$_2$)$_o$—Ar wherein Ar is phenyl or naphthyl and o is 0, 1, or 2.

13. A compound according to claim 5, wherein R is —(CH$_2$)$_0$—Ar wherein Ar is phenyl or naphthyl and o is 0, 1, or 2.

14. A compound according to claim 1, wherein R is methyl or ethyl.

15. A compound according to claim 2, wherein R is methyl or ethyl.

16. A compound according to claim 4, wherein R is methyl or ethyl.

17. A compound according to claim 5, wherein R is methyl or ethyl.

18. A compound according to claim 5, wherein said compound is selected from:

3-cyano-1H-indole-7-carboxylic acid, methyl 3-hydroxyimino-1H-indole-7-carboxylate, ethyl 3-hydroxyimino-1H-indole-7-carboxylate, tert-butyl 3-hydroxyimino-1H-indole-7-carboxylate, benzyl 3-hydroxyimino-1H-indole-7-carboxylate, methyl 3-cyano-1H-indole-7-carboxylate, ethyl 3-cyano-1H-indole-7-carboxylate, tert-butyl 3-cyano-1H-indole-7-carboxylate, benzyl 3-cyano-1H-indole-7-carboxylate, methyl 3-bromo-1H-indole-7-carboxylate, ethyl 3-bromo-1H-indole-7-carboxylate, tert-butyl 3-bromo-1H-indole-7-carboxylate, benzyl 3-bromo-1H-indole-7-carboxylate, methyl 3-iodo-1H-indole-7-carboxylate, ethyl 3-iodo-1H-indole-7-carboxylate, tert-butyl 3-iodo-1H-indole-7-carboxylate, benzyl 3-iodo-1H-indole-7-carboxylate, and salts thereof.

19. A compound according to claim 18, wherein said compound is selected from:

3-cyano-1H-indole-7-carboxylic acid, methyl 3-hydroxyimino-1H-indole-7-carboxylate, ethyl 3-hydroxyimino-1H-indole-7-carboxylate, tert-butyl 3-hydroxyimino-1H-indole-7-carboxylate, benzyl 3-hydroxyimino-1H-indole-7-carboxylate, methyl 3-cyano-1H-indole-7-carboxylate, ethyl 3-cyano-1H-indole-7-carboxylate, tert-butyl 3-cyano-1H-indole-7-carboxylate, benzyl 3-cyano-1H-indole-7-carboxylate, methyl 3-bromo-1H-indole-7-carboxylate, ethyl 3-bromo-1H-indole-7-carboxylate, tert-butyl 3-bromo-1H-indole-7-carboxylate, benzyl 3-bromo-1H-indole-7-carboxylate, methyl 3-iodo-1H-indole-7-carboxylate, ethyl 3-iodo-1H-indole-7-carboxylate, tert-butyl 3-iodo-1H-indole-7-carboxylate, and benzyl 3-iodo-1H-indole-7-carboxylate.

20. A process for the preparation of (3-cyano-1H-indol-7-yl)[4-(4-fluorophenethyl)piperazin-1-yl]methanone of formula I

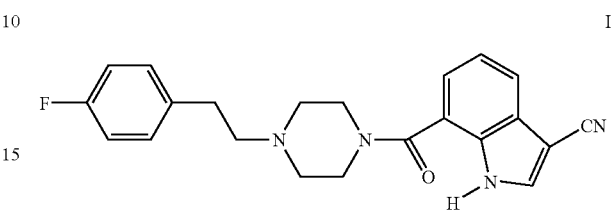

and salts thereof, said process comprising:

(A) (1) formylating an indole ester of the formula II

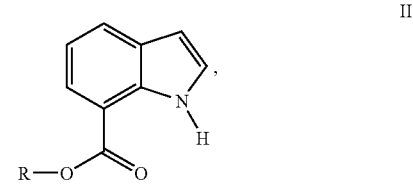

in which

R is an alkyl group having from 1 to 6 carbon atoms or arylalkyl;

(2) reacting the resultant formyl ester of formula III

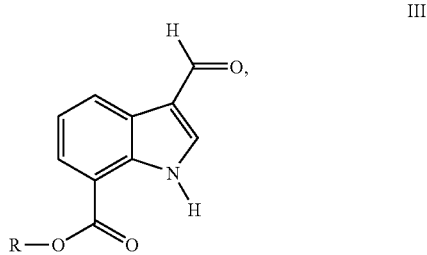

with hydroxylamine to give an oxime derivative of formula IV

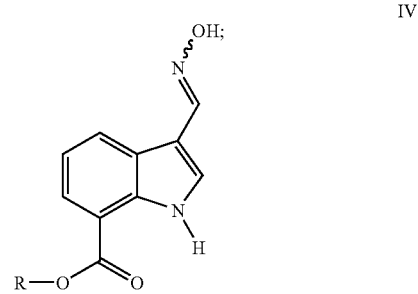

(3) converting the oxime of formula IV into a cyanoindole ester of formula V

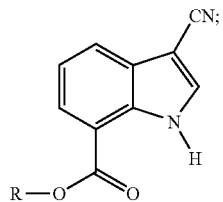

V (4) saponifying the ester of formula V to give 3-cyano-1H-indole-7-carboxylic acid, (5) reacting the 3-cyano-1H-indole-7-carboxylic acid with 1-[2-(4-fluoro-phenyl)ethyl]piperazine or a salt thereof to give the compound of the formula I, and (6) optionally converting the resultant base of formula I into one of its salts by treatment with an acid; or (B) (1) halo genating an indole ester of the formula II

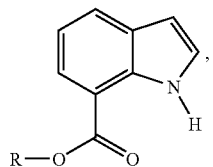

II in which

R is an alkyl group having from 1 to 6 carbon atoms or arylalkyl;

(2) converting the halogen of the resultant ester of formula VI

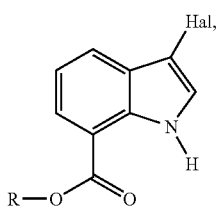

VI wherein Hal is Cl, Br or I, into a to form a cyano group with the ester group being saponifying at the same time to obtain 3-cyano-1H-indole-7-carboxylic acid, (3) reacting the 3-cyano-1H-indole-7-carboxylic acid with 1-[2-(4-fluoro-phenyl)ethyl]piperazine or a salt thereof to give the compound of the formula I, and (4) optionally converting the resultant base of formula I into one of its salts by treatment with an acid.

21. A process according to claim 20, wherein steps (1) to (3) are carried out as a one-pot synthesis.

22. A process according to claim 20, wherein in step (4), the ester of the formula V is converted into a compound of formula I by aminolysis using 1-[2-(4-fluorophenyl)ethyl]piperazine or a salt thereof.

23. A process according to claim 20, wherein said 3-cyano-1H-indole-7-carboxylic acid is prepared by halogenation of an indole ester of formula II

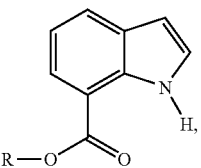

II to give a compound of the formula VI

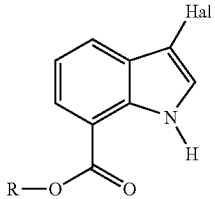

VI in which

R is an alkyl group having from 1 to 6 carbon atoms or arylalkyl, and

Hal is Cl, Br or I, followed by cyanation.

24. A process according to claim 20, wherein R is ethyl.

25. A process according to claim 20, said 3-cyano-1H-indole-7-carboxylic acid is reacted with the dihydrochloride is 1-[2-(4-fluorophenyl)ethyl]piperazine.

26. A process according to claim 20, wherein in step (5) the compound of formula I is the base (3-cyano-1H-indol-7-yl)[4-(4-fluorophenethyl)-piperazin-1-yl]methanone, and said base is converted into its hydrochloride in step (6).

* * * * *

UNITED STATES PATENT AND TRADEMARK OFFICE
CERTIFICATE OF CORRECTION

PATENT NO. : 7,312,342 B2 Page 1 of 1
APPLICATION NO. : 10/466991
DATED : December 25, 2007
INVENTOR(S) : Andreas Bathe It is certified that error appears in the above-identified patent and that said Letters Patent is hereby corrected as shown below:

Column 14, line 5, after formula IV, replace ";" with -- , --
Column 14, line 25, after formula V, replace ";" with -- , --
Column 17, line 22, reads "halo genating" should read -- halogenating --
Column 17, line 51, delete "a to form"
Column 18, line 46, reads "claim 20, said" should read -- claim 20, wherein said --

Signed and Sealed this

Seventeenth Day of November, 2009

David J. Kappos
*Director of the United States Patent and Trademark Office*